(12) United States Patent
Etienne et al.

(10) Patent No.: US 9,452,370 B2
(45) Date of Patent: Sep. 27, 2016

(54) PROCESS AND APPARATUS FOR SIMULATED COUNTER-CURRENT CHROMATOGRAPHIC SEPARATION FOR HIGH-PRODUCTIVITY PRODUCTION OF PARAXYLENE

(71) Applicant: IFP ENERGIES NOUVELLES, Rueil-Malmaison (FR)

(72) Inventors: Pascal Etienne, Estrablin (FR); Philibert Leflaive, Mions (FR); Damien Leinekugel Le Cocq, Lyons (FR); Catherine Laroche, Vernaison (FR)

(73) Assignee: IFP ENERGIES NOUVELLES, Ruel-Malmaison (FR)

( * ) Notice: Subject to any disclaimer, the term of this patent is extended or adjusted under 35 U.S.C. 154(b) by 385 days.

(21) Appl. No.: 14/093,599

(22) Filed: Dec. 2, 2013

(65) Prior Publication Data

US 2014/0155672 A1    Jun. 5, 2014

(30) Foreign Application Priority Data

Dec. 3, 2012 (FR) ...................................... 12 03277

(51) Int. Cl.
| | | |
|---|---|---|
| *C07C 7/12* | (2006.01) | |
| *C07C 7/13* | (2006.01) | |
| *B01D 15/18* | (2006.01) | |
| *B01J 20/18* | (2006.01) | |
| *B01J 20/28* | (2006.01) | |

(52) U.S. Cl.
CPC ....... *B01D 15/1828* (2013.01); *B01D 15/1842* (2013.01); *B01J 20/186* (2013.01); *B01J 20/2803* (2013.01); *B01J 20/28011* (2013.01); *C07C 7/13* (2013.01)

(58) Field of Classification Search
CPC .................................. C07C 7/12; C07C 7/13
USPC ......................................... 585/828, 827, 825
See application file for complete search history.

(56) References Cited

U.S. PATENT DOCUMENTS

| | | |
|---|---|---|
| 6,376,734 B1 | 4/2002 | Magne-Drisch et al. |
| 7,812,208 B2 | 10/2010 | Cheng et al. |
| 2013/0053610 A1 | 2/2013 | Leinekugel Le Cocq et al. |

FOREIGN PATENT DOCUMENTS

| | | |
|---|---|---|
| FR | 2693186 A1 | 1/1994 |
| FR | 2795407 A1 | 12/2000 |
| FR | 2979252 A1 | 3/2013 |

OTHER PUBLICATIONS

Search Report dated Jul. 24, 2013 issued in corresponding FR 1203277application (pp. 1-2).

*Primary Examiner* — Thuan D Dang
(74) *Attorney, Agent, or Firm* — Millen White Zeland and Branigan, PC; John Sopp; Anthony Zelano

(57) ABSTRACT

The present invention describes a process for the separation of xylenes in simulated counter-current utilising at least one adsorber with a limited cumulated total height (Hcu) of adsorbent and a superficial velocity (Vsl) of less than 2 cm/s.

15 Claims, No Drawings

PROCESS AND APPARATUS FOR SIMULATED COUNTER-CURRENT CHROMATOGRAPHIC SEPARATION FOR HIGH-PRODUCTIVITY PRODUCTION OF PARAXYLENE

FIELD OF THE INVENTION

The invention relates to the field of separation of paraxylene (PX) from a charge of aromatic hydrocarbons essentially comprising 8 carbon atoms by contact between liquid and solid phases. As that type of charge can be difficult to separate by distillation, a family of adsorption processes and associated apparatuses which are known by the name of chromatographic separation processes or apparatuses or "simulated movable bed" or "simulated counter-current", which hereinafter we shall refer to with the abbreviation SCC, is then used.

The invention to an SCC separation process making it possible to obtain PX in a state of high purity, that is to say at least 99.7%, in a single step.

EXAMINATION OF THE PRIOR ART

SCC separation is well known in the state of the art. In general a process for the separation of paraxylene operating in a simulated counter-current mode comprises at least four zones and possibly five or six, each of those zones being formed by a certain number of successive beds and each zone being defined by its position between a feed point and a draw-off point.

Typically an SCC unit for the production of paraxylene is fed with at least one charge F to be fractionated (containing paraxylene and other aromatic C8 isomers) and a desorbent D, sometimes referred to as the eluent (generally paradiethylbenzene or toluene). At least one raffinate R containing the isomers of paraxylene and desorbent and an extract E containing paraxylene and desorbent are withdrawn from said unit.

The feed and draw-off points are modified in the passage of time, being displaced in the same direction by a value corresponding to a bed. The shifts in the different injection or draw-off points can be either simulated or non-simulated, as is taught by patent FR2785196. The process in accordance with that second mode of operation is referred as VARICOL.

Conventionally, 4 different chromatographic zones are defined in an SCC unit.

Zone 1: zone for desorption of the paraxylene, between injection of the desorbent D and withdrawal of the extract E.

Zone 2: zone for desorption of the isomers of the paraxylene, between the withdrawal of the extract E and injection of the charge F to be fractionated.

Zone 3: zone for adsorption of the paraxylene, between injection of the charge and withdrawal of the raffinate R.

Zone 4: zone between withdrawal of the raffinate R and injection of the desorbent D.

As described by Lim et al (2010, Ind. Eng. Chem. Res. Vol. 49, p. 3316-3327) and Kurup et al (Ind. Eng. Chem. Res. 2005, 44, 5703-5714), the process for separation of paraxylene by SCC is generally composed of 24 beds distributed among two adsorbers each of 12 beds, each bed being of an adsorbent solid height of about 1.1 m. Thus the combined height of adsorbent solid in relation to the whole of the adsorber, which will be referred to hereinafter as Hcu, is about 26 m.

Recent research in the field of adsorbents for separation of paraxylene made it possible to develop adsorbents with improved transfer properties. For example patents FR2903978 and FR2925366 disclose zeolitic adsorbents based on small crystals of zeolite X or LSX exchanged with barium or barium and potassium.

U.S. Pat. No. 7,812,208 also claims a process for the separation of paraxylene by bringing it into contact with an adsorbent without a binder (referred to as "binderless" in English terminology) comprising a first portion of zeolite X involving a crystal size of between 500 nanometres and 1.5 microns, and a second portion of zeolite X having a crystal size either less than 500 nanometres or greater than 1.8 microns.

The quoted patent specifies that this type of adsorbent has improved material transfer properties. Implementation of those adsorbents involving an improved transfer is preferably performed at low temperature and/or with a reduced cycle time.

In regard to the latter point, it is specified that in a typical simulated movable bed unit having 24 beds (2 adsorbers each containing 12 beds), with all other things being equal, a reduction in the cycle time corresponds to an increase in productivity.

It is in fact known to the man skilled in the art that, for a given industrial adsorber, a reduction in the cycle time is accompanied by an equivalent increase in the total of the liquid flow rates in the adsorber, this being in order to maintain the solid and liquid flow rate ratios constant in the different zones of the simulated movable bed.

The amount of paraxylene produced, therefore the productivity expressed as kg of $PX/m^3/h$, thus increases by an amount which is also proportional, to the detriment of purity and/or yield.

It is this that is illustrated in FIG. 6 of U.S. Pat. No. 7,812,208 in which it can be seen that, for a given adsorbent, the reduction in the cycle time induces a reduction in yield (that is to say the amount of PX issuing in the extract with respect to the amount of PX introduced in the charge).

It is also possible to see from that same Figure that the use of an adsorbent with improved transfer properties permits a significant reduction in the cycle time (therefore internal liquid flow rates, and productivity) with an iso-yield.

To sum up, for implementation of adsorbents with small crystals and having improved transfer properties the prior art recommends either an increase in the flow rates (incoming and outgoing, as well as the internal recycling flow rate) associated with a reduction in the cycle times to use that increase in transfer directly, or operation at low temperature (that is to say below 175° C.), which makes it possible to increase the capacity and selectivity of the adsorbent.

BRIEF DESCRIPTION OF THE INVENTION

The process according to the invention proposes improved implementation of the production of paraxylene in a state of high purity utilising a cumulated height of adsorbent solid in relation to all of the adsorber or adsorbers (referred to as Hcu), which is less than that conventionally used in a 24 bed adsorber, and carrying out the process with a mean superficial velocity on each adsorber of between 1 cm/s and 2 cm/s, the latter being defined as the mean recycling flow rate by volume at the temperature of the process divided by the area of the section of the adsorber.

It has in fact been surprisingly noted that the use of a cumulated height of adsorbent solid in relation to the whole of the adsorbers (Hcu) of between 6 m and 21 m, combined with a mean superficial velocity on each adsorber (Vsl) of between 1 cm/s and 2 cm/s, made it possible to produce high-purity paraxylene, that is to say of a purity of higher than 99.7%, with improved levels of performance in relation to conventional 24 bed implementation.

The significant reduction in the cumulated height (Hcu) makes it possible in a particular case to operate the unit with a single adsorber, which gives rise to a significant gain in terms of capital investment in relation to a process composed of two adsorbers.

The beds constituting an adsorber are all identical and the total number of adsorption beds is generally between 6 and 18 beds and preferably between 8 and 15 beds.

More precisely the present invention can be defined as a process for separation of paraxylene by simulated countercurrent (SCC) chromatography from a charge F essentially comprising paraxylene and its aromatic C8 isomers, said process utilising a zeolitic adsorbent solid based on zeolite crystals X and a certain proportion of non-zeolitic phase, in which the zeolite crystals X have an average diameter by number of less than or equal to 1.7 μm, preferably less than or equal to 1.5 μm, and still more preferably less than or equal to 1.2 μm, said process being carried out in at least one adsorber divided into 4 chromatographic zones defined in the following fashion:

Zone 1: zone for desorption of the paraxylene, between injection of the desorbent D and withdrawal of the extract E.
Zone 2: zone for desorption of the isomers of the paraxylene, between the withdrawal of the extract E and injection of the charge F to be fractionated.
Zone 3: zone for adsorption of the paraxylene, between injection of the charge and withdrawal of the raffinate R.
Zone 4: zone between withdrawal of the raffinate R and injection of the desorbent D, said process being characterised in that it has a cumulated height of adsorbent solid in relation to the whole of the adsorbers (Hcu) of between 6 m and 21 m and that the mean superficial velocity over each adsorber (Vsl) is between 1 cm/s and 2 cm/s.

In a preferred variant of the xylene separation process according to the invention the atomic ratio Si/Al of the adsorbent is preferably such that $1.05<Si/Al<1.55$, preferably such that $1.10 \leq Si/Al<1.55$ and still more preferably such that $1.10 \leq Si/Al<1.30$.

In another preferred variant of the xylene separation process according to the invention the adsorbent solid used is a zeolitic adsorbent shaped by agglomeration, with crystals whose average diameter by number is between 0.1 and 1.5 microns and preferably between 0.1 and 1.2 microns.

In another variant of the xylene separation process according to the invention the mean distribution over a cycle of the cumulated height (Hcu) of adsorbent solid is as follows:
the cumulated height of adsorbent solid in zone 1 on average over a cycle is 21%±5% of (Hcu),
the cumulated height of adsorbent solid in zone 2 on average over a cycle is 37.5%±5% of (Hcu),
the cumulated height of adsorbent solid in zone 3 on average over a cycle is 29%±5% of (Hcu),
the cumulated height of adsorbent solid in zone 4 on average over a cycle is 12.5%±5% of (Hcu).
Preferably the total number of beds is between 6 and 18 beds and still more preferably the total number of beds is between 8 and 15 beds.

According to the present invention the total number of beds can be distributed over one or more adsorbers.

Preferably the height of a bed is between 0.7 m and 1.40 m.

In a preferred variant the number of adsorber used in the process according to the invention is 1.

When there are a plurality of adsorbers they are disposed in series in the direction in which the following three characteristics are observed:
the last bed of the n-th adsorber is connected to the first bed of the adsorber n+1, by way of a line containing at least one recirculation pump and optionally other items of equipment such as a flowmeter, a pressure sensor, etc.,
the last bed of the last adsorber is connected to the first bed of the first adsorber, by way of a line containing at least one recirculation pump and optionally other items of equipment such as a flowmeter, a pressure sensor, etc,
the whole of the adsorbers has at least 1 point for introduction of the charge, 1 point for introduction of the eluent, 1 point for drawing off the raffinate and 1 point for drawing off the extract.

Preferably the operating conditions of the adsorption step of the process according to the invention are as follows:
temperature 100° C. to 250° C., preferably 120° C. to 180° C.,
pressure between the bubble pressure of the xylenes at the temperature of the process and $30 \times 10^5$ Pa,
ratio of the flow rate of desorbent in relation to the flow rate of charge of between 0.7 and 2.5,
recycling rate of 2.0 to 12, preferably 2.5 to 6 (the recycling rate being defined as the ratio between the mean flow rate flowing in the different beds of an adsorber in relation to the flow rate of injection of the charge into that adsorber), and
water content in liquid phase of between 70 and 140 ppm (by weight) and preferably between 80 and 120 ppm (by weight).

In a preferred variant of the xylene separation process according to the invention the adsorbent solid has a small proportion of amorphous phase, that is to say less than 5% by weight.

Finally according to another preferred variant of the process according the invention the ignition loss of the adsorbent solid measured at 900° C. is between 4.0% and 7.7% by weight and preferably between 4.7% and 6.7% by weight.

DETAILED DESCRIPTION OF THE INVENTION

The present invention concerns a process for the separation of paraxylene by simulated counter-current (SCC) chromatography from a charge F essentially comprising paraxylene and its aromatic C8 isomers, said process being carried out in an adsorber and being characterised in that it has a cumulated height of adsorbent solid in relation to the whole of the adsorbers (Hcu) of between 6 and 21 m and the mean superficial velocity over each adsorber (Vsl) is between 1 and 2 cm/s.

A cumulated height of adsorbent solid in relation to all of the adsorbers (Hcu) of greater than 21 m makes operation in a single adsorber expensive for reasons of pressure drops and dimensions of the adsorber.

In addition the process according to the invention aims to treat substantial flow rates of charge to be treated, making it necessary to have an internal diameter for each adsorber of between 4 and 10 m.

A cumulated height of adsorbent solid in relation to all of the adsorbers (Hcu) of less than 6 m gives rise to problems in terms of distribution of liquid.

In addition a linear superficial velocity (Vsl) which is low (that is to say less than 1 cm/s) generally does not make it possible to achieve high productivity and is likely to cause distribution problems, in particular for large-diameter adsorbers.

Conversely a superficial velocity (Vsl) of greater than 2 cm/s can give rise to a movement of the adsorbent at the surface of the beds, which is harmful to the levels of performance and can cause bed attrition.

According to a feature of the process the adsorbent used in the adsorption step can comprise a zeolite of faujasite type exchanged with barium or barium and potassium.

Preferably the adsorbent of the process according to the invention is a zeolitic adsorbent based on zeolite crystals X and non-zeolitic phase, with a content of barium oxide BaO of greater than 33%, preferably ranging from 33% to 42%, and more advantageously again ranging from 35% to 38% by weight with respect to the total weight of the adsorbent.

The content of potassium oxide $K_2O$ is generally less than 9%, still more preferably ranging from 0 to 2% and advantageously ranging from 0 to 1% by weight with respect to the total weight of adsorbent.

The total content of oxides of alkali metal or alkaline-earth ions other than barium and potassium is preferably less than 5% and preferably ranging from 0 to 2% and advantageously ranging from 0 to 1% by weight with respect to the total weight of the adsorbent.

The adsorbent of the process according to the invention is also preferably a zeolitic adsorbent based on zeolite crystals X and non-zeolitic phase in which the zeolite crystals X are of an average diameter by number of less than or equal to 1.7 µm, preferably less than or equal to 1.5 µm and still more preferably less than or equal to 1.2 µm.

Very preferably the zeolite crystals X are of an average diameter by number ranging from 0.1 µm to 1.5 µm and advantageously ranging from 0.1 to 1.2 µm.

The non-zeolitic phase is generally formed by an amorphous residual binder.

The atomic ratio Si/Al of the adsorbent is preferably such that $1.05<Si/Al<1.55$, preferably such that $1.10 \leq Si/Al<1.55$ and still more preferably such that $1.10 \leq Si/Al<1.30$.

Estimating the average diameter by number of the zeolite crystals X contained in the adsorbent solid is effected by observation with a scanning electron microscope (SEM) on a polished section in retrodiffused electron mode with chemical contrast.

In order to estimate the size of the zeolite crystals on the samples an assembly of images involving a magnification of at least 5000 is produced. The diameter of at least 200 crystals is then measured by means of dedicated software (Smile View, LoGraMi).

The average diameter by number is then calculated from the granulometric distribution by applying the standard ISO 9276-2:2001. For that calculation reference is made to the document "Representation of data obtained by granulometric analysis"—Part 2: calculation of the sizes/average diameters of particles from granulometric distribution.

In the quoted document the expression "average diameter by number" is used for the zeolite crystals, which we retain in the context of the present invention.

The paraxylene separation process according to the invention can use an adsorbent containing a substantial fraction of binder, that is to say typically between 10 and 25%, but also an adsorbent without binder (referred to as "binderless" in English terminology), that is to say containing an amount of amorphous phase of typically less than 1% or again an adsorbent containing a reduced binder content (referred to as "binderlow" in English terminology), that is to say containing an amount of amorphous phase of typically between 1 and 5%.

Those last two types of adsorbents can be obtained after a step for zeolitisation of the binder. Still more preferably the adsorbent has a proportion of amorphous phase which is low, that is to say less than 5% by weight.

The ignition loss measured at 900° C. is between 4.0% and 7.7% by weight and preferably between 4.7% and 6.7% by weight.

The preferred desorbent is paradiethylbenzene. However other desorbents such as toluene, paradifluorobenzene or diethylbenzenes as a mixture may also be suitable. Paradiethylbenzene is preferably recommended for its facility for it to be recovered by distillation and for its strong affinity for the adsorbent.

According to another feature of the process the operating conditions of the adsorption step are as follows:
  temperature 100° C. to 250° C., preferably 120° C. to 180° C.,
  pressure between the bubble pressure of the xylenes at the temperature of the process and $30 \times 10^5$ Pa,
  ratio of the flow rate of desorbent in relation to the flow rate of charge of between 0.7 and 2.5,
  recycling rate of 2.0 to 12, preferably 2.5 to 6, the recycling rate being defined as the ratio between the mean flow rate flowing in the different beds of an adsorber in relation to the flow rate of injection of the charge into that adsorber, and
  water content in liquid phase of between 70 and 140 ppm (by weight) and preferably between 80 and 120 ppm (by weight).

The total number of beds of the process according to the invention is preferably between 6 and 18 beds and still more preferably between 8 and 15 beds distributed over one or more adsorbers.

The number of beds will be so adjusted that each bed is preferably of a height of between 0.70 m and 1.40 m.

The 4 chromatographic zones are generally defined in the following fashion:
  Zone 1: zone for desorption of the paraxylene, between injection of the desorbent D and withdrawal of the extract E.
  Zone 2: zone for desorption of the isomers of the paraxylene, between the withdrawal of the extract E and injection of the charge F to be fractionated.
  Zone 3: zone for adsorption of the paraxylene, between injection of the charge and withdrawal of the raffinate R.
  Zone 4: zone between withdrawal of the raffinate R and injection of the desorbent D.

According to another feature of the process of the invention the mean distribution over a cycle of the cumulated height of adsorbent solid is as follows:
  the cumulated height of adsorbent solid in zone 1 on average over a cycle is 21%±5% of (Hcu),
  the cumulated height of adsorbent solid in zone 2 on average over a cycle is 37.5%±5% of (Hcu),
  the cumulated height of adsorbent solid in zone 3 on average over a cycle is 29%±5% of (Hcu), the cumulated height of adsorbent solid in zone 4 on average over a cycle is 12.5%±5% of (Hcu).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 12/03.277, filed Dec. 3, 2012 are incorporated by reference herein.

EXAMPLES ACCORDING TO THE INVENTION

The invention will be better appreciated from reading the two examples which follow.

Example 1

Process According to the Prior Art

An SCC adsorber is considered, formed by 24 beds, of a length of 1.1 m and with an internal radius of 4 m, with a charge injection, a desorbent injection, an extract withdrawal and a raffinate withdrawal.

The adsorbent used is a zeolitic solid of type BaX forming 1 μm crystals shaped as balls measuring 0.53 mm.

The desorbent is paradiethylbenzene.

The temperature is 175° C. and the pressure is 15 bars. The water content is 95 ppm (by weight).

The charge is composed of 21.6% of paraxylene, 20.8% of orthoxylene, 47.9% of metaxylene and 9.7% of ethylbenzene.

The SCC adsorber is formed by 24 beds distributed over two adsorbers, the beds being separated by distributor plates.

Corresponding to each distributor plate is an injection system and a drawing-off system.

The rinsing device used is the device with modulated tapped-off fluid flow as described in WO 2010/020715. Synchronicity is 100% in each zone.

The displacements of the different injection or drawing-off points are simultaneous. The beds are distributed in 4 chromatographic zones according to the configuration: 5/9/7/3.

The charge and desorbent injection flow rates (defined considering a reference temperature of 40° C.) are as follows:

15.44 m$^3$·min$^{-1}$ for the charge, and
19.51 m$^3$·min$^{-1}$ for the desorbent.

The extract drawing-off flow rate is 10.03 m$^3$·min$^{-1}$. The permutation period employed is 40.7 seconds.

The mean superficial velocity over the whole of an adsorber is 2.07 cm/s.

By simulation a paraxylene purity of 99.81% and a paraxylene yield of 97.6% is obtained, with a productivity of 124.5 kg$_{PX}$·h$^{-1}$·m$^{-3}$.

Example 2

Process According to the Invention

An SCC adsorber is considered, formed by 14 beds distributed over an adsorber, each bed being of a length of 1.1 m, namely an Hcu of 15.4 m and with an internal radius of 4 m, with a charge injection, a desorbent injection, an extract withdrawal and a raffinate withdrawal.

The adsorbent used is a zeolitic solid of type BaX forming 1 μm crystals shaped as balls measuring 0.53 mm. The desorbent is paradiethylbenzene. The adsorbent and the desorbent are therefore identical to those of the Example according to the prior art.

The temperature is 175° C. and the pressure is 15 bars. The water content is 95 ppm (by weight).

The charge is composed of 21.6% of paraxylene, 20.8% of orthoxylene, 47.9% of metaxylene and 9.7% of ethylbenzene.

The SCC adsorber is formed by 14 beds separated by distributor plates. Corresponding to each distributor plate is an injection system and a drawing-off system.

The rinsing device used is the device with modulated tapped-off fluid flow as described in WO 2010/020715. Synchronicity is 100% in each zone.

The displacements of the different injection or drawing-off points are simultaneous. The beds are distributed in 4 chromatographic zones according to the configuration: 3/5/4/2.

The charge and desorbent injection flow rates (defined considering a reference temperature of 40° C.) are as follows:

9.01 m$^3$·min$^{-1}$ for the charge, and
11.38 m$^3$·min$^{-1}$ for the desorbent.

The extract drawing-off flow rate is 5.85 m$^3$·min$^{-1}$. The permutation period employed is 69.8 seconds.

The mean superficial velocity over the whole of an adsorber is 1.20 cm/s-1.

By simulation a paraxylene purity of 99.83% and a paraxylene yield of 98.2% is obtained, with a productivity of 125.3 kg$_{PX}$·h$^{-1}$·m$^{-3}$. The gain in purity, paraxylene yield and productivity is therefore entirely significant in relation to the prior art.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for separation of paraxylene by simulated counter-current (SCC) chromatography from a charge F essentially comprising paraxylene and its aromatic C8 isomers, comprising contacting the charge with a zeolitic adsorbent solid based on zeolite crystals X and a non-zeolitic phase, in which the zeolite crystals X have an average diameter by number of between 0.1 and 1.5 microns, said process using at least one adsorber divided into 4 chromatographic zones defined in the following fashion:

Zone 1: zone for desorption of the paraxylene, between injection of a desorbent D and withdrawal of an extract E;

Zone 2: zone for desorption of the isomers of the paraxylene, between the withdrawal of the extract E and injection of the charge F to be fractionate;

Zone 3: zone for adsorption of the paraxylene, between injection of the charge and withdrawal of a raffinate R;

Zone 4: zone between withdrawal of the raffinate R and injection of the desorbent D; the number of adsorption beds being between 6 and 18, the beds all being identical, and the height of each bed being between 0.7 m and 1.4 m, said process being characterised in that it has a cumulated height of adsorbent solid in relation to the different adsorber or adsorbers (Hcu) of between 6 m and 21 m and that the mean superficial velocity over each adsorber (Vsl) is between 1 cm/s and 2 cm/s, said superficial velocity being defined as the mean recycling flow rate by volume at the temperature of the process divided by the area of the section of the adsorber, and the cumulated height (Hcu) of adsorbent solid being distributed in the following fashion:

the cumulated height of adsorbent solid in zone 1 on average over a cycle is 21%±5% of Hcu, the cumulated height of adsorbent solid in zone 2 on average over a cycle is 37.5%±5% of Hcu, the cumulated height of adsorbent solid in zone 3 on average over a cycle is 29%±5% of Hcu, the cumulated height of adsorbent solid in zone 4 on average over a cycle is 12.5%±5% of Hcu.

2. A process for the separation of xylenes according to claim 1 wherein the atomic ratio Si/Al of the adsorbent is such that 1.05<Si/Al<1.55.

3. A process for the separation of xylenes according to claim 1 wherein the adsorbent solid comprises zeolite X having a content of barium oxide BaO ranging from 33% to 42% by weight with respect to the total weight of the adsorbent.

4. A process for the separation of xylenes according to claim 1 wherein the diameter of each adsorber is between 4 m and 10 m.

5. A process for the separation of xylenes according to claim 1 wherein the number of adsorbers used is 1.

6. A process for the separation of xylenes according to claim 1 wherein the operating conditions of the adsorption step are as follows:

temperature 100° C. to 250° C., pressure between the bubble pressure of the xylenes at the temperature of the process and $30 \times 10^5$ Pa, ratio of the flow rate of desorbent in relation to the flow rate of charge of between 0.7 and 2.5, recycling rate of 2.0 to 12 (the recycling rate being defined as the ratio between the mean flow rate flowing in the different beds of an adsorber in relation to the flow rate of injection of the charge into that adsorber), and water content in liquid phase of between 70 and 140 ppm (by weight).

7. A process for the separation of xylenes according to claim 1 wherein the adsorbent solid has a proportion of amorphous phase of less than 5% by weight.

8. A process according to claim 1 wherein the ignition loss of the adsorbent solid measured at 900° C. is between 4.0% and 7.7% by weight.

9. A process according to claim 1 wherein the zeolite crystals X have an average diameter by number of between 0.1 and 1.2 microns.

10. A process according to claim 1 wherein the number of adsorption beds being between 8 and 15.

11. A process according to claim 1 wherein the atomic ratio Si/Al of the adsorbent is such that 1.10≤Si/Al<1.55.

12. A process according to claim 1 wherein the atomic ratio Si/Al of the adsorbent is such that 1.10≤Si/Al<1.30.

13. A process according to claim 1 wherein the adsorbent solid comprises zeolite X having a content of barium oxide BaO ranging from 35% to 38% by weight with respect to the total weight of the adsorbent.

14. A process according to claim 6 wherein the operating conditions of the adsorption step are as follows:

temperature 120° C. to 180° C., recycling rate of 2.5 to 6, and water content in liquid phase of between 80 and 120 ppm (by weight).

15. A process according to claim 1 wherein the ignition loss of the adsorbent solid measured at 900° C. is between 4.7% and 6.7% by weight.

* * * * *